(12) United States Patent
Rekhi et al.

(10) Patent No.: US 8,992,973 B2
(45) Date of Patent: Mar. 31, 2015

(54) CONTROLLED RELEASE COMPOSITIONS COMPRISING A COMBINATION OF ISOSORBIDE DINITRATE AND HYDRALAZINE HYDROCHLORIDE

(75) Inventors: Gurvinder Singh Rekhi, Suwanee, GA (US); Richard Sidwell, Cumming, GA (US); Sharon Hamm, Atlanta, GA (US)

(73) Assignee: Alkermes Science One Limited, Dublin (IE)

( * ) Notice: Subject to any disclaimer, the term of this patent is extended or adjusted under 35 U.S.C. 154(b) by 0 days.

(21) Appl. No.: 13/606,915

(22) Filed: Sep. 7, 2012

(65) Prior Publication Data
US 2013/0004573 A1 Jan. 3, 2013

Related U.S. Application Data

(63) Continuation of application No. 13/278,787, filed on Oct. 21, 2011, now abandoned, which is a continuation of application No. 11/262,672, filed on Oct. 31, 2005, now abandoned.

(51) Int. Cl.
| | | |
|---|---|---|
| *A61K 9/54* | (2006.01) | |
| *A61K 9/16* | (2006.01) | |
| *A61K 9/50* | (2006.01) | |
| *A61K 31/403* | (2006.01) | |
| *A61K 31/4745* | (2006.01) | |
| *A61K 31/58* | (2006.01) | |
| *A61K 31/704* | (2006.01) | |

(52) U.S. Cl.
CPC ............. *A61K 9/5084* (2013.01); *A61K 31/403* (2013.01); *A61K 31/4745* (2013.01); *A61K 31/58* (2013.01); *A61K 31/704* (2013.01); *A61K 9/5026* (2013.01); *A61K 9/5078* (2013.01)
USPC .......................................... 424/458; 424/490

(58) Field of Classification Search
None
See application file for complete search history.

(56) References Cited

U.S. PATENT DOCUMENTS

| 4,794,001 A | 12/1988 | Mehta et al. |
| 4,868,179 A | 9/1989 | Cohn |
| 6,228,398 B1 | 5/2001 | Devane et al. |
| 6,635,281 B2 | 10/2003 | Wong et al. |
| 2003/0185888 A1 | 10/2003 | Wong et al. |
| 2004/0170684 A1 | 9/2004 | Baichwal et al. |
| 2004/0185097 A1 | 9/2004 | Kannan et al. |
| 2004/0198789 A1 | 10/2004 | Leonardi et al. |
| 2005/0175695 A1 | 8/2005 | Castan et al. |

FOREIGN PATENT DOCUMENTS

| EP | 0396425 A2 | 11/1990 |
| WO | 02/34303 A1 | 5/2002 |

OTHER PUBLICATIONS

U.S. Appl. No. 11/262,672 Advisory Action dated Sep. 11, 2009.
U.S. Appl. No. 11/262,672 Decision on Appeal dated Aug. 23, 2011.
U.S. Appl. No. 11/262,672 Examiners Answer dated Jul. 30, 2010.
U.S. Appl. No. 11/262,672 Final Office Action dated Apr. 29, 2009.
U.S. Appl. No. 11/262,672 Non Final Office Action dated Nov. 4, 2009.
U.S. Appl. No. 11/262,672 Non Final Office Action dated Jul. 24, 2008.
U.S. Appl. No. 11/262,672 Notice of Decision from Pre-Appeal Brief Review dated Mar. 5, 2010.
EP Appln. 06826636.0—European Search Report dated Dec. 16, 2011.
EP Appln. 06826637.8—European Search Report dated Dec. 16, 2011.
Ludden et al., Relative Bioavailability of Immediate- and Sustained-Release Hydralazine Formulations, Journal of Pharmaceutical Sciences, vol. 77, No. 12, Dec. 1968, pp. 1026-1032.
U.S. Appl. No. 11/373,629 Non Final Office Action dated Feb. 3, 2009.
U.S. Appl. No. 11/373,629 Final Rejection dated Jul. 16, 2009.
U.S. Appl. No. 11/373,629 Non Final Rejection dated Jan. 27, 2010.
U.S. Appl. No. 11/373,629 Final Rejection dated Aug. 30, 2010.
U.S. Appl. No. 11/373,629 Final Rejection dated Dec. 22, 2010.
U.S. Appl. No. 11/373,629 Non Final Rejection dated Nov. 3, 2011.
U.S. Appl. No. 11/373,629 Final Rejection dated Jun. 29, 2012.
U.S. Appl. No. 13/278,787 Final Rejection dated Mar. 7, 2012.
PCT/US06/41625 Search Report dated May 10, 2007.
PCT/US06/41625 Written Opinion dated Jul. 18, 2007.
PCT/US06/41624 Search Report dated May 10, 2007.
PCT/US06/41624 Written Opinion dated Jul. 13, 2007.

*Primary Examiner* — Trevor Love
(74) *Attorney, Agent, or Firm* — Fox Rothschild LLP

(57) ABSTRACT

The invention relates to a controlled release composition comprising a combination of isosorbide dinitrate and hydralazine, such as hydralazine hydrochloride, that in operation delivers the drug in a pulsed or multi-modal manner for the treatment of angina, ischaemic heart disease, arterial hypertension and related disease conditions. Preferably, the isosorbide dinitrate and hydralazine hydrochloride can be released from the dosage form in an erodable, diffusion and/or osmotic-controlled release profile.

18 Claims, No Drawings

CONTROLLED RELEASE COMPOSITIONS COMPRISING A COMBINATION OF ISOSORBIDE DINITRATE AND HYDRALAZINE HYDROCHLORIDE

CROSS REFERENCE OT RELATED APPLICATIONS

This application is a continuation of U.S. patent application Ser. No. 13/278,787 filed Oct. 21, 2011, which is a continuation of U.S. patent application Ser. No. 11/262,672 filed Oct. 31, 2005, both of which are incorporated herein by reference in their entireties.

FIELD OF INVENTION

The present invention relates to novel compositions for the treatment of patients suffering from angina, ischaemic heart disease, arterial hypertension and related disease conditions. In particular, the present invention relates to novel dosage forms for the controlled delivery of combinations of isosorbide dinitrate and hydralazine, or a salt or derivative thereof, and methods of treatment using the same.

BACKGROUND OF INVENTION

Isosorbide Dinitrate, classified as a vasodilator, anti-anginal compound, is chemically known as 1,4:3,6-dianhydro-D-glucitol dinitrate; 1,4:3,6-dianhydrosorbitol 2,5-dinitrate; dinitrosorbide; sorbide dinitrate; and sorbide nitrate. It has a CAS number of 87-33-2. Isosorbide dinitrate has a chemical formula of $C_6H_8N_2O_8$, and a molecular weight of 236.1.

The chemical structure of isosorbide dinitrate is shown below:

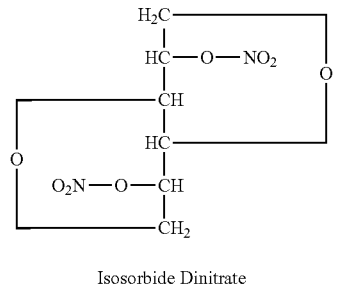

Isosorbide Dinitrate

Isosorbide dinitrate is a fine white to ivory-white odorless crystalline solid. It is sparingly soluble in water (1.0 g/900 ml); freely soluble in acetone, chloroform, alcohol and ether, and has a melting point of 70° C. Isosorbide dinitrate is a synthetic substance prepared from sorbitol. Diluted isosorbide dinitrate is a mixture of isosorbide dinitrate (usually 20-50%) with lactose, mannitol, or excipients added to minimize the risk of explosion. It may contain up to about 1% of a suitable stabilizer such as ammonium phosphate.

Isosorbide dinitrate is commercially available, for example, under the trade names DILATRATE®-SR (Schwarz Pharma, Milwaukee, Wis.); ISORDIL® and ISOR-DILR TITRADOSE® (Wyeth Laboratories Inc., Philadelphia, Pa.); and SORBITRATE® (Zeneca Pharmaceuticals, Wilmington, Del.). Isosorbide dinitrate is also commercially available under such trade names as Cedocard-5, Cedocard-10, Cedocard-20, Cedocard Retard, Cedocard IV (Tillotts, UK), Isoket, Isoket 10, Isoket 20, Isoket Retard, Isoket 0.1% (Schwartz, UK), Isordil, Isordil Tembids (Ayerst, UK), Sorbichew, Sorbitrate (Stuart, UK), Vascardin (Nicholas, UK), Soni-Slo (Lipha Rona, UK); Conducil, Corosorbide, Maycor, Sigillum, Surantol, Vasodilat (Argentina); Carvasin, Isotrate (Australia); Sorbidilat (Belgium); Coronex (Canada); Risordan (France); Cardis, Corovliss, IsoMack, Maycor, Nitrol, Nitrosorbon, Sorbidilat, Vermicet (Germany); Carvasin, Nitrosorbide, (Italy); Directan, Nitrol (Japan); Isorbid (Mexico); Sorbaugil (Norway, Sweeden); IsoMack, Myorexon, Sorbidilat (Switzerland); Iso-Bid, Iso-D, Isotrate, Sorbide, Sorquad, Vasotrate (USA).

Isosorbide dinitrate is used principally for management of ischaemic heart disease by reducing the number, duration and severity of episodes of angina pectoris. It is effective for angina (e.g., stable effort angina, mixed angina, unstable angina and vasospastic or variant angina). Isosorbide dinitrate is used in acute myocardial infarction in control of ischaemic pain, reduction of elevated blood pressure and in the treatment of pulmonary edema and congestive cardiac failure. It is also useful in the treatment of severe hypertension.

Therapeutic isosorbide dinitrate dosages for adults for relief of acute attacks of angina, generally range from about 2.5 mg to about 10 mg. For long term management of ischaemic heart disease dosing ranges from about 30 mg to about 240 mg per day. Starting doses for the treatment of angina pectoris may be about 2.5 mg to about 10 mg every 2 to 3 hours, with dosages gradually increased up to about 10 mg to about 40 mg every 6 hours.

Hydralazine (including its salts, such as hydralazine hydrochloride) is classified as a vasodilator, antihypertensive compound. Hydralazine, also known as 1-hydrazinophatalazine; has a CAS number of 86-54-4. Hydralazine hydrochloride, also known as 1-hydrazinophtalazine hydrochloride; has a CAS number of 304-20-1. Hydralazine has the chemical structure of $C_8H_8N_4$, and hydralazine hydrochloride has the chemical structure of $C_8H_8N_4 \cdot HCl$.

The chemical formula of hydralazine and hydralazine hydrochloride are shown below:

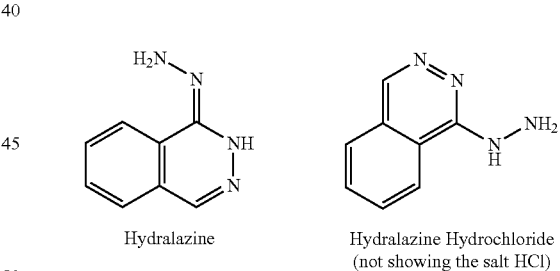

Hydralazine     Hydralazine Hydrochloride
(not showing the salt HCl)

Hydralazine hydrochloride has a white to off-white substance color and is a crystalline powder. It is an odorless to almost odorless compound. It is soluble in water (1 in 25), slightly soluble in ethanol (1 in 500) and in methanol; practically insoluble in ether or chloroform. A 2% solution in water has a pH of about 3.5 to about 4.2.

Hydralazine hydrochloride is commercially available from, for example, Lederle Standard Products of Pearl River, N.Y. and Par Pharmaceuticals Inc. of Spring Valley, N.Y. Hydralazine hydrochloride is branded under several trade names, such as Alphapress, Apresolin, Apresolina, Apresoline, Dralzine, Hidralazina, Hydralazine Hydrochloride Tablets USP 23, Hydralazine Injection BP 1993, Hydralazine Tablets BP 1993, Hydrapress, Hyperphen, Ipolina, Lowpress, Nepresol, Novo-Hylazin, Rolazine, Slow-Apresoline, and Supress.

Hydralazine, including its pharmaceutically acceptable salt forms, e.g., hydralazine hydrochloride, is useful in the treatment of arterial hypertension (primary; malignant; pulmonary; pre-eclampsia and eclampsia), congestive heart failure, pulmonary hypertension in chronic obstructive pulmonary disease, and aortic regurgitation. Therapeutic dosages for adults range generally from about 10 mg four times a day for the first 2 to 4 days, increasing to about 25 mg 4 times a day for the remainder of the first week. For the subsequent weeks, dosages may be increased up to about 50 mg 4 times a day. For heart failure dosages may range up to about 800 mg daily or more.

Isosorbide dinitrate and hydralazine hydrochloride combinations, and/or like compounds, have been disclosed, for example, in U.S. Pat. No. 4,868,179 to Cohn for "Method of Reducing Mortality Associated with Congestive Heart Failure Using Hydralazine and Isosorbide Dinitrate"; U.S. Pat. No. 6,465,463 to Cohn et al. for "Methods of Treating and Preventing Congestive Heart Failure with Hydralazine Compounds and Isosorbide Dinitrate or Isosorbide Mononitrate"; U.S. Pat. No. 6,635,273 to Loscalzo et al. for "Methods of Treating Vascular Diseases Characterized by Nitric Oxide Insufficiency"; and United States Patent Application No. 2004/0204371 to Cohn et al. for "Kits of Hydralazine Compounds and Isosorbide Dintrate and/or Isosorbide Mononitrate".

The combination of isosorbide dinitrate and hydralazine hydrochloride has been developed by Nitromed, Inc. of Lexington, Mass. under the trade name BiDil®. The combination has been reported to provide a synergistic therapeutic effect for patients over the individual use of each of the active agents. BiDil® is generally administered three times a day in dosages of isosorbide dinitrate/hydralazine hydrochloride, respectively from about 60/112.5 to about 120/225 mg.

The present invention relates to a composition for the controlled-release of a combination of isosorbide, including salts, derivatives and metabolites thereof, such as isosorbide dinitrate, (referred to herein as "isosorbide dinitrate") and hydralazine, or salt or derivative thereof, such as hydralazine hydrochloride (referred to herein as "hydralazine hydrochloride"). In particular, the present invention relates to a composition that in operation delivers an active isosorbide dinitrate and hydralazine hydrochloride combination in a pulsatile or in a constant zero order release manner. The present invention further relates to solid oral dosage forms containing such a controlled release composition. The present invention is particularly applicable for multiparticulate formulations of a combination product for isosorbide dinitrate and hydralazine hydrochloride, providing a twice-a-day or once daily administration. In particular, the present invention provides immediate-release pellets and/or beads for isosorbide dinitrate and hydralazine hydrochloride, e.g., using powder layering technology or standard Glatt Wurster Process, and sustained-release pellets and/or beads for isosorbide dinitrate and hydralazine hydrochloride, e.g., using various polymers or combination of polymers to provide various release rates ranging from about 6 hours to about 12 hours or about 12 hours to about 24 hours with or without lag time. In one particularly preferred embodiment, these multiparticulates are encapsulated in a hard gelatin capsule to give an isosorbide dinitrate content of about 30 mg to about 120 mg and a hydralazine content of about 50 mg to about 250 mg ranging for about 12 hour to about 24 hour dosing. Representative proportions of the immediate release (IR) beads vary from about 10% to about 60%, with representative proportions of complementary sustained release (SR) beads varying from about 30% to about 90%. The IR/SR combination may be blended for ease of manufacture or may be individually dosed with capsules. Additionally, the multiparticulates manufactured can be tabletted using suitable excipients to give appropriate isosorbide dinitrate and hydralazine content, as stated above.

DESCRIPTION OF THE INVENTION

The plasma profile associated with the administration of a drug compound may be described as a "pulsatile profile" in which pulses of high isosorbide dinitrate and hydralazine hydrochloride concentration, interspersed with low concentration troughs, are observed. A pulsatile profile containing two peaks may be described as "bimodal". A pulsatile profile containing two or more peaks may be described as "multimodal". Similarly, a composition or a dosage form which produces such a profile upon administration may be said to exhibit "pulsed release" of the isosorbide dinitrate and hydralazine hydrochloride.

Conventional frequent dosage regimes in which an immediate release (IR) dosage form is administered at periodic intervals typically gives rise to a pulsatile plasma profile. In this case, a peak in the plasma drug concentration is observed after administration of each IR dose with troughs (regions of low drug concentration) developing between consecutive administration time points. Such dosage regimes (and their resultant pulsatile plasma profiles) have particular pharmacological and therapeutic effects associated with them. For example, the wash out period provided by the fall off of the plasma concentration of the active between peaks has been thought to be a contributing factor in reducing or preventing patient tolerance to various types of drugs.

Multiparticulate modified controlled release compositions similar to those disclosed herein are disclosed and claimed in the U.S. Pat. Nos. 6,228,398 and 6,730,325 to Devane et al; both of which are incorporated by reference herein. Additional disclosures of a spheroidal oral drug absorption system for multiparticulate drug delivery for controlling the release and absorption rate of particular active agents are found in U.S. Pat. No. 4,863,742 to Panoz et al.; U.S. Pat. No. 4,917,899 to Geoghegan et al.; and U.S. Pat. No. 6,066,339 Stark et al., the disclosures of which are herein incorporated by reference. Typically this spheroidal oral drug absorption system includes microshperoidal beads having representative diameters of from about 0.5 mm to about 2.0 mm, with each bead providing a miniature controlled absorption system, allowing individualized release rates for the isosorbide dinitrate and hydralazine hydrochloride. Such beads may be dispensed in dispensing systems, such as capsules, sprinkles and tablets.

Accordingly, it is an object of the present invention to provide a multiparticulate modified release composition containing isosorbide dinitrate and hydralazine hydrochloride which in operation produces a plasma profile substantially similar to the plasma profile produced by the administration of three or more IR dosage forms given sequentially.

It is a further object of the invention to provide a multiparticulate modified release composition which in operation delivers isosorbide dinitrate and hydralazine hydrochloride in a pulsatile manner.

Another object of the invention is to provide a multiparticulate modified release composition which substantially mimics the pharmacological and therapeutic effects produced by the administration of three or more IR dosage forms given sequentially.

Another object of the present invention is to provide a multiparticulate modified release composition which substantially reduces or eliminates the development of patient tolerance to isosorbide dinitrate and hydralazine hydrochloride of the composition.

Another object of the invention is to provide a multiparticulate modified release composition in which a first portion of an isosorbide dinitrate and hydralazine hydrochloride combination is released immediately upon administration and a second portion of the active ingredient is released rapidly after an initial delay period in a multi-modal manner.

Another object of the present invention is to formulate the dosage forms as erodable formulations, diffusion-controlled formulations, and osmotic-controlled formulations that deliver the drug in a zero order fashion for about 12 to about 24 hours.

Another object of the invention is to provide a multiparticulate modified release composition capable of releasing isosorbide dinitrate and hydralazine hydrochloride in a bimodal or multi-modal manner in which a first portion of the active is released either immediately or after a delay time to provide a pulse of drug release and one or more additional portions of the active are released each after a respective lag time to provide additional pulses of drug release.

Another object of the invention is to provide solid oral dosage forms comprising a multiparticulate modified release composition of the present invention.

Other objects of the invention include provision of a once daily dosage form of an isosorbide dinitrate and hydralazine hydrochloride which, in operation, produces a plasma profile substantially similar to the plasma profile produced by the administration of three immediate release dosage forms given sequentially and a method for treatment of angina, ischaemic heart disease, arterial hypertension and related disease conditions based on the administration of such a dosage form.

DETAILED DESCRIPTION OF THE INVENTION

A. Multiparticulate Controlled Release Isosorbide Dinitrate and Hydralazine Hydrochloride Compositions The above objects are realized by a controlled release composition having a first component comprising a first population of isosorbide dinitrate and hydralazine hydrochloride, and a second and subsequent component comprising a second and subsequent population of isosorbide dinitrate and hydralazine hydrochloride particles. The ingredient-containing particles of the second and subsequent component are coated with a modified release coating. Alternatively or additionally, the second and subsequent population of isosorbide dinitrate and hydralazine hydrochloride-containing particles further comprises a modified release matrix material. Following oral delivery, the composition in operation delivers the isosorbide dinitrate and hydralazine hydrochloride in a first order (pulsatile) or zero order manner.

In a preferred embodiment, the controlled release composition of the present invention comprises a first component which is an immediate release component.

The modified release coating applied to the second and subsequent population of isosorbide dinitrate and hydralazine hydrochloride causes a lag time between the release of active from the first population of active isosorbide dinitrate and hydralazine hydrochloride-containing particles and the release of active from the second and subsequent population of active isosorbide dinitrate and hydralazine hydrochloride-containing particles. Similarly, the presence of a modified release matrix material in the second and subsequent populations of active isosorbide dinitrate and hydralazine hydrochloride-containing particles causes a lag time between the release of isosorbide dinitrate and hydralazine hydrochloride from the first population of isosorbide dinitrate and hydralazine hydrochloride-containing particles and the release of active ingredient from the second population of active ingredient containing particles. Similarly, the presence of a modified release matrix material in the second and subsequent population of active isosorbide dinitrate and hydralazine hydrochloride-containing particles causes a lag time between the release of isosorbide dinitrate and hydralazine hydrochloride from the second population of isosorbide dinitrate and hydralazine hydrochloride-containing particles and the release of active ingredient from the third population of active ingredient containing particles. The duration of the lag time may be varied by altering the composition and/or the amount of the modified release coating and/or altering the composition and/or amount of modified release matrix material utilized. Thus, the duration of the lag time can be designed to mimic a desired plasma profile.

Because the plasma profile produced by the controlled release composition upon administration is substantially similar to the plasma profile produced by the administration of two or more IR dosage forms given sequentially, the controlled release composition of the present invention is particularly useful for administering isosorbide dinitrate and hydralazine hydrochloride for which patient tolerance may be problematical. This controlled release composition is therefore advantageous for reducing or minimizing the development of patient tolerance to the active ingredient in the composition.

In a preferred embodiment of the present invention, isosorbide dinitrate and hydralazine hydrochloride and the composition in operation delivers the isosorbide dinitrate and hydralazine hydrochloride in a multi-modal pulsatile or zero order manner. Such a pulsatile composition in operation produces a plasma profile which substantially mimics that obtained by the sequential administration of two IR doses as, for instance, that found in a typical treatment regimen. The present invention further relates to a controlled release composition comprising isosorbide dinitrate and hydralazine hydrochloride which in operation produced a plasma profile that eliminates the "peaks" and "troughs" produced by the administration of two or more IR dosage forms given sequentially if such a profile is beneficial. This type of profile can be obtained using a controlled release mechanism that allows for "zero-order" delivery.

The present invention also provides solid oral dosage forms comprising the novel compositions of the present invention.

The term "particulate" as used herein refers to a state of matter which is characterized by the presence of discrete particles, pellets, beads or granules irrespective of their size, shape or morphology. The term "multiparticulate" as used herein means a plurality of discrete or aggregated particles, pellets, beads, granules or mixture thereof, irrespective of their size, shape or morphology.

The term "modified release" as used herein with respect to the coating or coating material or used in any other context, means release which is not immediate release and is taken to encompass controlled release, sustained release and delayed release.

The term "time delay" as used herein refers to the duration of time between administration of the composition and the release of the isosorbide dinitrate and hydralazine hydrochloride from a particular component.

The term "lag time" as used herein refers to the time between delivery of the isosorbide dinitrate and hydralazine hydrochloride from one component and the subsequent delivery isosorbide dinitrate and hydralazine hydrochloride from another component.

The term "erodable" as used herein refers to formulations which may be worn away, diminished, or deteriorated by the action of substances within the body.

The term "diffusion controlled" as used herein refers to formulations which may spread as the result of their spontaneous movement, for example, from a region of higher to one of lower concentration.

The term "osmotic controlled" as used herein refers to formulations which may spread as the result of their movement through a semi-permeable membrane into a solution of higher concentration that tends to equalize the concentrations of the formulation on the two sides of the membrane.

The active ingredient in each component may be the same or different. For example, a composition may comprise a first component containing isosorbide dinitrate and hydralazine hydrochloride, and the second component may comprise a second active ingredient which would be desirable for combination therapies. Indeed, two or more active ingredients may be incorporated into the same component when the active ingredients are compatible with each other. A drug compound present in one component of the composition may be accompanied by, for example, an enhancer compound or a sensitizer compound in another component of the composition, in order to modify the bioavailability or therapeutic effect of the drug compound.

As used herein, the term "enhancer" refers to a compound which is capable of enhancing the absorption and/or bioavailability of an active ingredient by promoting net transport across the GIT in an animal, such as a human. Enhancers include but are not limited to medium chain fatty acids; salts, esters, ethers and derivatives thereof, including glycerides and triglycerides; non-ionic surfactants such as those that can be prepared by reacting ethylene oxide with a fatty acid, a fatty alcohol, an alkylphenol or a sorbitan or glycerol fatty acid ester; cytochrome P450 inhibitors, P-glycoprotein inhibitors and the like; and mixtures of two or more of these agents.

Furthermore, as stated herein, "stabilizers" refers to a compound which is capable of enhancing the stability of an active ingredient e.g. stability enhancers, pH modifiers, chelating agents, antioxidants, free radical sequestrants, etc. . . . Examples of stabilizers include but are not limited to edetic acid and salts thereof, citric acid and salts thereof, and ascorbic acid, fumaric acid and salts thereof.

The proportion of the isosorbide dinitrate and hydralazine hydrochloride contained in each component may be the same or different depending on the desired dosing regime. The isosorbide dinitrate and hydralazine hydrochloride are present in the first component and in the second component in any amount sufficient to elicit a therapeutic response. The isosorbide dinitrate and hydralazine hydrochloride, when applicable, may be present either in the form of one substantially optically pure enantiomer or as a mixture, racemic or otherwise, of enantiomers. The isosorbide dinitrate and hydralazine hydrochloride are preferably present individually in a composition in an amount of from about 0.1 to about 500 mg, preferably in the amount of from about 1 about 100 mg. The isosorbide dinitrate and hydralazine hydrochloride are each preferably present in the first component in an amount of from about 0.5 to about 60 mg; more preferably the isosorbide dinitrate and hydralazine hydrochloride are each present in the first component in an amount of from about 2.5 to about 30 mg. The isosorbide dinitrate and hydralazine hydrochloride are present in the subsequent components in an amount within a similar range to that described for the first component.

The time release characteristics for the delivery of theisosorbide dinitrate and hydralazine hydrochloride from each of the components may be varied by modifying the composition of each component, including modifying any of the excipients or coatings which may be present. In particular, the release of the isosorbide dinitrate and hydralazine hydrochloride may be controlled by changing the composition and/or the amount of the modified release coating on the particles, if such a coating is present. If more than one modified release component is present, the modified release coating for each of these components may be the same or different. Similarly, when modified release is facilitated by the inclusion of a modified release matrix material, release of the active ingredient may be controlled by the choice and amount of modified release matrix material utilized. The modified release coating may be present, in each component, in any amount that is sufficient to yield the desired delay time for each particular component. The modified release coating may be preset, in each component, in any amount that is sufficient to yield the desired time lag between components.

The lag time or delay time for the release of the isosorbide dinitrate and hydralazine hydrochloride from each component may also be varied by modifying the composition of each of the components, including modifying any excipients and coatings which may be present. For example, the first component may be an immediate release component wherein the isosorbide dinitrate and hydralazine hydrochloride are released immediately upon administration. Alternatively, the first component may be, for example, a time-delayed immediate release component in which the isosorbide dinitrate and hydralazine hydrochloride are released substantially in their entirety immediately after a time delay. The second and subsequent component may be, for example, a time-delayed immediate release component as just described or, alternatively, a time-delayed sustained release or extended release component in which the isosorbide dinitrate and hydralazine hydrochloride are released in a controlled fashion over an extended period of time.

As will be appreciated by those skilled in the art, the exact nature of the plasma concentration curve will be influenced by the combination of all of these factors just described. In particular, the lag time between the delivery (and thus also the on-set of action) of the isosorbide dinitrate and hydralazine hydrochloride in each component may be controlled by varying the composition and coating (if present) of each of the components. Thus by variation of the composition of each component (including the amount and nature of the active ingredient(s)) and by variation of the lag time, numerous release and plasma profiles may be obtained. Depending on the duration of the lag time between the release of the isosorbide dinitrate and hydralazine hydrochloride from each component and the nature of the release of the isosorbide dinitrate and hydralazine hydrochloride from each component (i.e. immediate release, sustained release etc.), the pulses in the plasma profile may be well separated and clearly defined peaks (e.g. when the lag time is long) or the pulses may be superimposed to a degree (e.g. in when the lag time is short).

In a preferred embodiment, the controlled release composition according to the present invention has an immediate release component and at least one modified release component, the immediate release component comprising a first population of active ingredient containing particles and the modified release component comprising second and subsequent populations of active ingredient containing particles. The second and subsequent modified release components may comprise a controlled release coating. Additionally or alternatively, the second and subsequent modified release components may comprise a modified release matrix material. In operation, administration of such a multiparticulate modified release composition having, for example, a single modified release component results in characteristic pulsatile plasma concentration levels of the isosorbide dinitrate and hydralazine hydrochloride in which the immediate release component of the composition gives rise to a first peak in the plasma profile and the modified release component gives rise to a second peak in the plasma profile. Embodiments of the invention comprising more than one modified release component give rise to further peaks in the plasma profile.

Such a plasma profile produced from the administration of a single dosage unit is advantageous when it is desirable to deliver two (or more) pulses of active ingredient without the need for administration of two (or more) dosage units. Additionally, in the case of treating angina, ischaemic heart disease, arterial hypertension and related disease conditions, it is particularly useful to have such a bimodal plasma profile. For example, a typical isosorbide dinitrate and hydralazine hydrochloride treatment regime consists of the administration of two doses of an immediate release dosage formulation given twelve hours apart. This type of regime has been found to be therapeutically effective and is widely used. As previously mentioned, the development of patient tolerance is an adverse effect sometimes associated with isosorbide dinitrate and hydralazine hydrochloride treatments. It is believed that the trough in the plasma profile between the two peak plasma concentrations is advantageous in reducing the development of patient tolerance by providing a period of wash out of the isosorbide dinitrate and hydralazine hydrochloride active.

In addition, a delivery system having a zero order or pseudo-zero order delivery that eliminates or minimizes the "peak" to "trough" ratio is also described.

Any coating material which modifies the release of the isosorbide dinitrate and hydralazine hydrochloride in the desired manner may be used. In particular, coating materials suitable for use in the practice of the present invention include but are not limited to polymer coating materials, such as cellulose acetate phthalate, cellulose acetate trimaletate, hydroxy propyl methylcellulose phthalate, polyvinyl acetate phthalate, ammonio methacrylate copolymers such as those sold under the Trade Mark Eudragit® RS and RL, poly acrylic acid and poly acrylate and methacrylate copolymers such as those sold under the Trade Mark Eudragit® S and L, polyvinyl acetaldiethylamino acetate, hydroxypropyl methylcellulose acetate succinate, shellac; hydrogels and gel-forming materials, such as carboxyvinyl polymers, sodium alginate, sodium carmellose, calcium carmellose, sodium carboxymethyl starch, polyvinyl alcohol, hydroxyethyl cellulose, methyl cellulose, gelatin, starch, and cellulose based cross-linked polymers—in which the degree of crosslinking is low so as to facilitate adsorption of water and expansion of the polymer matrix, hydroxypropyl cellulose, hydroxypropyl methylcellulose, polyvinylpyrrolidone, crosslinked starch, microcrystalline cellulose, chitin, aminoacryl-methacrylate copolymer (Eudragit® RS-PM, Rohm & Haas), pullulan, collagen, casein, agar, gum arabic, sodium carboxymethyl cellulose, (swellable hydrophilic polymers) poly(hydroxyalkyl methacrylate) (m. wt. about 5 k-5,000 k), polyvinylpyrrolidone (m. wt. about 10 k-360 k), anionic and cationic hydrogels, polyvinyl alcohol having a low acetate residual, a swellable mixture of agar and carboxymethyl cellulose, copolymers of maleic anhydride and styrene, ethylene, propylene or isobutylene, pectin (m. wt. about 30 k-300 k), polysaccharides such as agar, acacia, karaya, tragacanth, algins and guar, polyacrylamides, Polyox(polyethylene oxides (m. wt. about 100 k-5,000 k), AquaKeep(acrylate polymers, diesters of polyglucan, crosslinked polyvinyl alcohol and poly N-vinyl-2-pyrrolidone, sodium starch glucolate (e.g. Explotab(; Edward Mandell C. Ltd.); hydrophilic polymers such as polysaccharides, methyl cellulose, sodium or calcium carboxymethyl cellulose, hydroxypropyl methyl cellulose, hydroxypropyl cellulose, hydroxyethyl cellulose, nitro cellulose, carboxymethyl cellulose, cellulose ethers, polyethylene oxides (e.g. Polyox®, Union Carbide), methyl ethyl cellulose, ethylhydroxy ethylcellulose, cellulose acetate, cellulose butyrate, cellulose propionate, gelatin, collagen, starch, maltodextrin, pullulan, polyvinyl pyrrolidone, polyvinyl alcohol, polyvinyl acetate, glycerol fatty acid esters, polyacrylamide, polyacrylic acid, copolymers of methacrylic acid or methacrylic acid (e.g. Eudragit®, Rohm and Haas), other acrylic acid derivatives, sorbitan esters, natural gums, lecithins, pectin, alginates, ammonia alginate, sodium, calcium, potassium alginates, propylene glycol alginate, agar, and gums such as arabic, karaya, locust bean, tragacanth, carrageens, guar, xanthan, scleroglucan and mixtures and blends thereof. As will be appreciated by the person skilled in the art, excipients such as plasticisers, lubricants, solvents and the like may be added to the coating. Suitable plasticisers include for example acetylated monoglycerides; butyl phthalyl butyl glycolate; dibutyl tartrate; diethyl phthalate; dimethyl phthalate; ethyl phthalyl ethyl glycolate; glycerin; propylene glycol; triacetin; citrate; tripropioin; diacetin; dibutyl phthalate; acetyl monoglyceride; polyethylene glycols; castor oil; triethyl citrate; polyhydric alcohols, glycerol, acetate esters, gylcerol triacetate, acetyl triethyl citrate, dibenzyl phthalate, dihexyl phthalate, butyl octyl phthalate, diisononyl phthalate, butyl octyl phthalate, dioctyl azelate, epoxidised tallate, triisoctyl trimellitate, diethylhexyl phthalate, di-n-octyl phthalate, di-i-octyl phthalate, di-i-decyl phthalate, di-n-undecyl phthalate, di-n-tridecyl phthalate, tri-2-ethylhexyl trimellitate, di-2-ethylhexyl adipate, di-2-ethylhexyl sebacate, di-2-ethylhexyl azelate, dibutyl sebacate.

When the modified release component comprises a modified release matrix material, any suitable modified release matrix material or suitable combination of modified release matrix materials may be used. Such materials are known to those skilled in the art. The term "modified release matrix material" as used herein includes hydrophilic polymers, hydrophobic polymers and mixtures thereof which are capable of modifying the release of isosorbide dinitrate and hydralazine hydrochloride dispersed therein in vitro or in viva Modified release matrix materials suitable for the practice of the present invention include but are not limited to microcrystalline cellulose, sodium carboxymethylcellulose, hydroxyalkylcelluloses such as hydroxypropylmethylcellulose and hydroxypropylcellulose, polyethylene oxide, alkylcelluloses such as methylcellulose and ethylcellulose, polyethylene glycol, polyvinylpyrrolidone, cellulose acteate, cellulose acetate butyrate, cellulose acteate phthalate, cellulose acteate trimellitate, polyvinylacetate phthalate, polyalkylmethacrylates, polyvinyl acetate and mixture thereof.

A controlled release composition according to the present invention may be incorporated into any suitable dosage form which facilitates release of the active ingredient in a pulsatile or zero order manner. Typically, the dosage form may be a blend of the different populations of isosorbide dinitrate and hydralazine hydrochloride-containing particles which make up the immediate release and the modified release components, the blend being filled into suitable capsules, such as hard or soft gelatin capsules. Alternatively, the different individual populations of active ingredient containing particles may be compressed (optionally with additional excipients) into mini-tablets which may be subsequently filled into capsules in the appropriate proportions. Another suitable dosage form is that of a multilayer tablet. In this instance the first component of the controlled release composition may be compressed into one layer, with the second component being subsequently added as a second layer of the multilayer tablet. The populations of isosorbide dinitrate and hydralazine hydrochloride-containing particles making up the composition of the invention may further be included in rapidly dissolving dosage forms such as an effervescent dosage form or a fast-melt dosage form.

The composition according to the invention comprises at least two populations of isosorbide dinitrate and hydralazine hydrochloride-containing particles which have different in-vitro dissolution profiles.

Preferably, in operation the composition of the invention and the solid oral dosage forms containing the composition release the isosorbide dinitrate and hydralazine hydrochloride such that substantially all of the isosorbide dinitrate and hydralazine hydrochloride contained in the first component is released prior to release of the isosorbide dinitrate and hydralazine hydrochloride from the second component. When the first component comprises an immediate release (IR) component, for example, it is preferable that release of the isosorbide dinitrate and hydralazine hydrochloride from the second component is delayed until substantially all the isosorbide dinitrate and hydralazine hydrochloride in the IR component has been released. Release of the isosorbide dinitrate and hydralazine hydrochloride from the second component may be delayed as detailed above by the use of a modified release coating(s) and/or a modified release matrix material.

More preferably, when it is desirable to minimize patient tolerance by providing a dosage regime which facilitates wash-out of a first dose of the isosorbide dinitrate and hydralazine hydrochloride from a patient's system, release of the isosorbide dinitrate and hydralazine hydrochloride from the second and subsequent component is delayed until substantially all of the isosorbide dinitrate and hydralazine hydrochloride contained in the first component has been released, and further delayed until at least a portion of the isosorbide dinitrate and hydralazine hydrochloride released from the first component has been cleared from the patient's system. In a preferred embodiment, release of the isosorbide dinitrate and hydralazine hydrochloride from the second component of the composition in operation is substantially, if not completely, delayed for a period of at least about two hours after administration of the composition.

The isosorbide dinitrate and hydralazine hydrochloride release of the drug from the second component of the composition in operation is substantially, if not completely, delayed for a period of at least about six hours, preferably about twelve hours, after administration of the composition.

B. Other Types of Controlled Release Isosorbide Dinitrate and Hydralazine Hydrochloride Compositions As described herein, the invention includes various types of controlled release systems by which the active drug may be delivered in a pulsatile or zero order manner. These systems include, but are not limited to: films with the drug in a polymer matrix (monolithic devices); the drug contained by the polymer (reservoir devices); polymeric colloidal particles or microencapsulates (microparticles, microspheres or nanoparticles) in the form of reservoir and matrix devices; drug contained by a polymer containing a hydrophilic and/or leachable additive e.g., a second polymer, surfactant or plasticizer, etc. to give a porous device, or a device in which the drug release may be osmotically "controlled" (both reservoir and matrix devices); enteric coatings (ionizable and dissolve at a suitable pH); (soluble) polymers with (covalently) attached 'pendant' drug molecules; devices where release rate is controlled dynamically: e.g., the osmotic pump.

The delivery mechanism of the present invention will control the rate of release of the drug. While some mechanisms will release the drug at a constant rate (zero order), others will vary as a function of time depending on factors such as changing concentration gradients or additive leaching leading to porosity, etc.

Polymers used in sustained release coatings are necessarily biocompatible, and ideally biodegradable. Examples of both naturally occurring polymers such as Aquacoat® (FMC Corporation, Food & Pharmaceutical Products Division, Philadelphia, USA) (ethylcellulose mechanically spheronised to sub-micron sized, aqueous based, pseudo-latex dispersions), and also synthetic polymers such as the Eudragit® (Röhm Pharma, Weiterstadt.) range of poly(acrylate, methacrylate) copolymers are known in the art.

1. Reservoir Devices

A typical approach to controlled release is to encapsulate or contain the drug entirely (e.g., as a core), within a polymer film or coat (i.e., microcapsules or spray/pan coated cores).

The various factors that can affect the diffusion process may readily be applied to reservoir devices (e.g., the effects of additives, polymer functionality {and, hence, sink-solution pH} porosity, film casting conditions, etc.) and, hence, the choice of polymer must be an important consideration in the development of reservoir devices. Modeling the release characteristics of reservoir devices (and monolithic devices) in which the transport of the drug is by a solution-diffusion mechanism therefore typically involves a solution to Fick's second law (unsteady-state conditions; concentration dependent flux) for the relevant boundary conditions. When the device contains dissolved active agent, the rate of release decreases exponentially with time as the concentration (activity) of the agent (i.e., the driving force for release) within the device decreases (i.e., first order release). If, however, the active agent is in a saturated suspension, then the driving force for release is kept constant (zero order) until the device is no longer saturated. Alternatively the release-rate kinetics may be desorption controlled, and a function of the square root of time.

Transport properties of coated tablets, may be enhanced compared to free-polymer films, due to the enclosed nature of the tablet core (permeant) which may enable the internal build-up of an osmotic pressure which will then act to force the permeant out of the tablet.

The effect of de-ionized water on salt containing tablets coated in poly(ethylene glycol) (PEG)-containing silicone elastomer, and also the effects of water on free films has been investigated. The release of salt from the tablets was found to be a mixture of diffusion through water filled pores, formed by hydration of the coating, and osmotic pumping. KCl transport through films containing just 10% PEG was negligible, despite extensive swelling observed in similar free films, indicating that porosity was necessary for the release of the KCl which then occurred by 'trans-pore diffusion.' Coated salt tablets, shaped as disks, were found to swell in de-ionized water and change shape to an oblate spheroid as a result of the build-up of internal hydrostatic pressure: the change in shape providing a means to measure the 'force' generated. As might be expected, the osmotic force decreased with increasing levels of PEG content. The lower PEG levels allowed water to be imbibed through the hydrated polymer; whilst the porosity resulting from the coating dissolving at higher levels of PEG content (about 20 to about 40%) allow the pressure to be relieved by the flow of KCl.

Methods and equations have been developed, which by monitoring (independently) the release of two different salts (e.g., KCl and NaCl) allowed the calculation of the relative magnitudes that both osmotic pumping and trans-pore diffusion contributed to the release of salt from the tablet. At low PEG levels, osmotic flow was increased to a greater extent than was trans-pore diffusion due to the generation of only a low pore number density: at a loading of 20%, both mechanisms contributed approximately equally to the release. The build-up of hydrostatic pressure, however, decreased the osmotic inflow, and osmotic pumping. At higher loadings of PEG, the hydrated film was more porous and less resistant to outflow of salt. Hence, although the osmotic pumping increased (compared to the lower loading), trans-pore diffusion was the dominant release mechanism. An osmotic release mechanism has also been reported for microcapsules containing a water soluble core.

2. Monolithic Devices (Matrix Devices)

Monolithic (matrix) devices are possibly the most common of the devices for controlling the release of drugs. This is possibly because they are relatively easy to fabricate, compared to reservoir devices, and there is not the danger of an accidental high dosage that could result from the rupture of the membrane of a reservoir device. In such a device the active agent is present as a dispersion within the polymer matrix, and they are typically formed by the compression of a polymer/drug mixture or by dissolution or melting. The dosage release properties of monolithic devices may be dependent upon the solubility of the drug in the polymer matrix or, in the case of porous matrixes, the solubility in the sink solution within the particle's pore network, and also the tortuosity of the network (to a greater extent than the permeability of the film), dependent on whether the drug is dispersed in the polymer or dissolved in the polymer. For low loadings of drug, (0 to 5% W/V) the drug will be released by a solution-diffusion mechanism (in the absence of pores). At higher loadings (5 to 10% W/V), the release mechanism will be complicated by the presence of cavities formed near the surface of the device as the drug is lost: such cavities fill with fluid from the environment increasing the rate of release of the drug.

It is common to add a plasticiser (e.g., a poly(ethylene glycol)), a surfactant, or adjuvant (i.e., an ingredient which increases effectiveness), to matrix devices (and reservoir devices) as a means to enhance the permeability (although, in contrast, plasticizers may be fugitive, and simply serve to aid film formation and, hence, decrease permeability—a property normally more desirable in polymer paint coatings). It was noted that the leaching of PEG increased the permeability of (ethyl cellulose) films linearly as a function of PEG loading by increasing the porosity, however, the films retained their barrier properties, not permitting the transport of electrolyte. It was deduced that the enhancement of their permeability was as a result of the effective decrease in thickness caused by the PEG leaching. This was evidenced from plots of the cumulative perminant flux per unit area as a function of time and film reciprocal thickness at a PEG loading of 50% W/W: plots showing a linear relationship between the rate of permeation and reciprocal film thickness, as expected for a (Fickian) solution-diffusion type transport mechanism in a homogeneous membrane. Extrapolation of the linear regions of the graphs to the time axis gave positive intercepts on the time axis: the magnitude of which decreased towards zero with decreasing film thickness. These changing lag times were attributed to the occurrence of two diffusional flows during the early stages of the experiment (the flow of the 'drug' and also the flow of the PEG), and also to the more usual lag time during which the concentration of permeant in the film is building-up. Caffeine, when used as a permeant, showed negative lag times. No explanation of this was forthcoming, but it was noted that caffeine exhibited a low partition coefficient in the system, and that this was also a feature of aniline permeation through polyethylene films which showed a similar negative time lag.

The effects of added surfactants on (hydrophobic) matrix devices has been investigated. It was thought that surfactant may increase the drug release rate by three possible mechanisms: (i) increased solubilization, (ii) improved 'wettability' to the dissolution media, and (iii) pore formation as a result of surfactant leaching. For the system studied (Eudragit® RL 100 and RS 100 plasticised by sorbitol, Flurbiprofen as the drug, and a range of surfactants) it was concluded that improved wetting of the tablet led to only a partial improvement in drug release (implying that the release was diffusion, rather than dissolution, controlled), although the effect was greater for Eudragit® RS than Eudragit® RL, whilst the greatest influence on release was by those surfactants that were more soluble due to the formation of 'disruptions' in the matrix allowing the dissolution medium access to within the matrix. This is of obvious relevance to a study of latex films which might be suitable for pharmaceutical coatings, due to the ease with which a polymer latex may be prepared with surfactant as opposed to surfactant-free. Differences were found between the two polymers—with only the Eudragit® RS showing interactions between the anionic/cationic surfactant and drug. This was ascribed to the differing levels of quaternary ammonium ions on the polymer.

Composite devices consisting of a polymer/drug matrix coated in a polymer containing no drug also exist. Such a device was constructed from aqueous Eudragit® latices, and was found to give zero order release by diffusion of the drug from the core through the shell. Similarly, a polymer core containing the drug has been produced, but coated this with a shell that was eroded by the gastric fluid. The rate of release of the drug was found to be relatively linear (a function of the rate limiting diffusion process through the shell) and inversely proportional to the shell thickness, whereas the release from the core alone was found to decrease with time.

3. Microspheres

Methods for the preparation of hollow microspheres ('microballoons') with the drug dispersed in the sphere's shell, and also highly porous matrix-type microspheres ('microsponges') have been described. The microsponges were prepared by dissolving the drug and polymer in ethanol. On addition to water, the ethanol diffused from the emulsion droplets to leave a highly porous particle.

The hollow microspheres were formed by preparing a solution of ethanol/dichloromethane containing the drug and polymer. On pouring into water, this formed an emulsion containing the dispersed polymer/drug/solvent particles, by a coacervation-type process, from which the ethanol (a good solvent for the polymer) rapidly diffused precipitating polymer at the surface of the droplet to give a hard-shelled particle enclosing the drug, dissolved in the dichloromethane. At this point, a gas phase of dichloromethane was generated within the particle which, after diffusing through the shell, was observed to bubble to the surface of the aqueous phase. The hollow sphere, at reduced pressure, then filled with water, which could be removed by a period of drying. (No drug was found in the water.) A suggested use of the microspheres was as floating drug delivery devices for use in the stomach.

4. Pendent Devices

A means of attaching a range of drugs such as analgesics and antidepressants, etc., by means of an ester linkage to poly(acrylate) ester latex particles prepared by aqueous emulsion polymerization has been developed. These latices when passed through an ion exchange resin such that the polymer end groups were converted to their strong acid form could 'self-catalyse' the release of the drug by hydrolysis of the ester link.

Drugs have been attached to polymers, and also monomers have been synthesized with a pendent drug attached. The research group have also prepared their own dosage forms in which the drug is bound to a biocompatible polymer by a labile chemical bond polyanhydrides prepared from a substituted anhydride (itself prepared by reacting an acid chloride with the drug: methacryloyl chloride and the sodium salt of methoxy benzoic acid) were used to form a matrix with a second polymer (Eudragit® RL) which released the drug on hydrolysis in gastric fluid. The use of polymeric Schiff bases suitable for use as carriers of pharmaceutical amines has also been described.

5. Enteric Films

Enteric coatings consist of pH sensitive polymers. Typically the polymers are carboxylated and interact (swell) very little with water at low pH, whilst at high pH the polymers ionize causing swelling, or dissolving of the polymer. Coatings can therefore be designed to remain intact in the acidic environment of the stomach (protecting either the drug from this environment or the stomach from the drug), but to dissolve in the more alkaline environment of the intestine.

6. Osmotically Controlled Devices

The osmotic pump is similar to a reservoir device but contains an osmotic agent (eg, the active agent in salt form) which acts to imbibe water from the surrounding medium via a semi-permeable membrane. Such a device, called the 'elementary osmotic pump', has been described. Pressure is generated within the device which forces the active agent out of the device via an orifice (of a size designed to minimize solute diffusion, whilst preventing the build-up of a hydrostatic pressure head which has the effect of decreasing the osmotic pressure and changing the dimensions {volume} of the device). Whilst the internal volume of the device remains constant, and there is an excess of solid (saturated solution) in the device, then the release rate remains constant delivering a volume equal to the volume of solvent uptake.

7. Electrically Stimulated Release Devices

Monolithic devices have been prepared using polyelectrolyte gels which swelled when, for example, an external electrical stimulus was applied, causing a change in pH. The release could be modulated, by the current, giving a pulsatile release profile.

8. Hydrogels

Hydrogels find a use in a number of biomedical applications, in addition to their use in drug matrices (e.g., soft contact lenses, and various 'soft' implants, etc.).

C. Methods of Using Controlled Release Isosorbide Dinitrate and Hydralazine Hydrochloride Compositions The present invention further provides a method of treating a patient suffering from angina, ischaemic heart disease, arterial hypertension and related disease conditions utilizing an isosorbide dinitrate and hydralazine hydrochloride composition of the present invention comprising the administration of a therapeutically effective amount of a solid oral dosage form of isosorbide dinitrate and hydralazine hydrochloride to provide a pulsed or multi-modal or zero order delivery of the isosorbide dinitrate and hydralazine hydrochloride. Advantages of the present invention include reducing the dosing frequency required by conventional multiple IR dosage regimes while still maintaining the benefits derived from a pulsatile plasma profile or eliminating or minimizing the "peak" to "trough" ratio. This reduced dosing frequency is advantageous in terms of patient compliance to have a formulation which may be administered at reduced frequency. The reduction in dosage frequency made possible by utilizing the present invention would contribute to reducing health care costs by reducing the amount of time spent by health care workers on the administration of drugs.

In the following examples, all percentages are weight by weight unless otherwise stated. The term "purified water" as used throughout the Examples refers to water that has been purified by passing it through a water filtration system. It is to be understood that the examples are for illustrative purposes only, and should not be interpreted as restricting the spirit and breadth of the invention, as defined by the scope of the claims that follow.

EXAMPLE 1

Multiparticulate Modified Release Composition Containing Isosorbide Dinitrate and Hydralazine Hydrochloride A multiparticulate modified release composition according to the present invention comprising an immediate release component and a modified release component containing isosorbide dinitrate and hydralazine hydrochloride is prepared as follows.

(a) Immediate Release Component.

A powder blend of isosorbide dinitrate or hydralazine hydrochloride is prepared according to any of the formulations given in Table 1.

A binder solution is prepared according to any of the formulations given in Table 2. A protective coating solution is prepared according to any of the formulations given in Table 3.

The powder blend is then layered onto a suitable substrate (e.g. sugar spheres or microcrystalline cellulose pellets) using a suitable binder solution to a level of approximately 400% solids weight gain using, for example, a Vector Granurex GX-40 (Vector Corporation, IA) rotary granulator apparatus to form the IR particles of the immediate release component. After the powder layering process is complete, the protective coating solution is coated onto the immediate release beads to a level of approximately 3% protective compound based on the mass of immediate release beads to be coated. A glidant powder blend consisting of talc, silicon dioxide or a combination of the two is simultaneously applied either separately or by suspension in the coating solution to reduce sticking and static. Examples of the final compositions of the immediate release beads are shown in Table 4.

TABLE 1

Powder blend compositions

| Ingredient | Amount (mg/g) | Amount (mg/g) | Amount (mg/g) |
| --- | --- | --- | --- |
| Diluted isosorbide dinitrate (40:60 mannitol/lactose) | — | — | 980 |
| Hydralazine hydrochloride | 980 | 800 | — |
| Talc | 10 | 10 | 10 |
| Silicon dioxide | 10 | 10 | 10 |
| Fumaric acid | — | 180 | — |

TABLE 2

Binder solution compositions

| Ingredient | Amount (mg/g) | Amount (mg/g) |
| --- | --- | --- |
| Isopropanol | 900 | 883.4 |
| Povidone | 100 | 100 |
| Edetate disodium | — | 16.6 |

TABLE 3

Protective coating solution compositions

| Ingredient | Amount (mg/g) |
| --- | --- |
| Isopropanol | 937.5 |
| Basic butylated methacrylate copolymers | 62.5 |

TABLE 4

Immediate release component compositions

| Ingredient | Amount (mg/g) | Amount (mg/g) | Amount (mg/g) | Amount (mg/g) |
| --- | --- | --- | --- | --- |
| Povidone | 56.6 | 56.6 | 56.6 | 56.6 |
| Edetate disodium | — | 9.4 | — | 9.4 |
| Isosorbide dinitrate | — | — | 273.7 | 270.0 |
| Mannitol/Lactose | — | — | 410.5 | 405.0 |
| Hydralazine hydrochloride | 684.2 | 551.0 | — | — |
| Talc | 21.1 | 21.0 | 21.1 | 21.0 |
| Silicon dioxide | 21.1 | 21.0 | 21.1 | 21.0 |
| Fumaric acid | — | 124.0 | — | — |
| Basic butylated methacrylate copolymers | 28.3 | 28.3 | 28.3 | 28.3 |
| Sugar spheres (30/35 mesh) | 188.7 | 188.7 | 188.7 | 188.7 |

(b) Modified Release Components

Isosorbide dinitrate and hydralazine hydrochloride containing delayed release particles are prepared by coating immediate release particles prepared according to Example 1(a) above with a modified release coating solution as detailed in Table 5. Talc is simultaneously applied during coating as a glidant and anti-static agent. The immediate release particles are coated to varying levels up to approximately 30% polymer weight gain using, for example, a rotary granulator or fluid bed apparatus. Example compositions of the modified release components representing 20% polymer weight gain are shown in Table 6.

TABLE 5

Modified release component coating solutions

| Ingredient | Amount (mg/g) |
| --- | --- |
| Isopropanol | 856 |
| Water | 24 |
| Methacrylic acid copolymers | 100 |
| Triethyl citrate | 20 |

TABLE 6

Modified release component compositions

| Ingredient | Amount (mg/g) | Amount (mg/g) | Amount (mg/g) | Amount (mg/g) |
| --- | --- | --- | --- | --- |
| Povidone | 39.3 | 39.3 | 39.3 | 39.3 |
| Edetate, disodium | — | 6.5 | — | 6.5 |
| Isosorbide dinitrate | — | — | 190.0 | 187.5 |
| Mannitol/Lactose | — | — | 285.1 | 281.2 |
| Hydralazine hydrochloride | 475.1 | 382.6 | — | — |
| Talc | 153.6 | 153.5 | 153.6 | 153.5 |
| Silicon dioxide | 14.7 | 14.6 | 14.7 | 14.6 |
| Fumaric acid | — | 86.1 | — | — |
| Basic butylated methacrylate copolymers | 19.7 | 19.7 | 19.7 | 19.7 |
| Sugar Spheres (30/35 mesh) | 131.0 | 131.0 | 131.0 | 131.0 |
| Methacrylic acid copolymers | 138.9 | 138.9 | 138.9 | 138.9 |
| Triethyl Citrate, USP | 27.8 | 27.8 | 27.8 | 27.8 |

(c) Encapsulation of Immediate and Delayed Release Particles.

The immediate and delayed release particles prepared according to Example 1(a) and (b) above are blended and encapsulated in size 0 hard gelatin capsules to an overall dosage strength of 60/112.5 mg of isosorbide dinitrate and hydralazine hydrochloride, respectively, using, for example, a Bosch GKF 400S encapsulation apparatus. The overall dosage strength of 60/112.5 mg isosorbide dinitrate and hydralazine hydrochloride, is made up of 40/75 mg from the immediate release component and 20/37.5 mg from the modified release component.

It will be apparent to those skilled in the art that various modifications and variations can be made in the methods and compositions of the present inventions without departing from the spirit or scope of the invention. Thus, it is intended that the present invention cover the modification and variations of the invention provided they come within the scope of the appended claims and their equivalents.

What is claimed is:

1. A solid pharmaceutical composition for oral administration comprising:
   a first population of active ingredient containing particles comprising isosorbide dinitrate, or a salt thereof, mannitol, and sugar spheres;
   a second population of active ingredient containing particles comprising hydralazine, or a salt thereof, sugar spheres, and at least one stabilizer selected from the group consisting of edetic acid, salts thereof, citric acid, and salts thereof;
   a third population of active ingredient containing particles comprising isosorbide dinitrate, or a salt thereof, mannitol, sugar spheres, and a protective coating selected from the group consisting of modified-release coatings and modified-release matrix coatings; and
   a fourth population of active ingredient containing particles comprising hydralazine, or a salt thereof, sugar spheres, at least one stabilizer selected from the group consisting of edetic acid, salts thereof, citric acid, and salts thereof, and a coating selected from the group consisting of modified-release coatings and modified-release matrix coatings;

wherein the amount of isosorbide dinitrate contained therein is in an amount of from about 0.1 mg to about 1 g; and wherein the amount of hydralazine contained therein is in an amount of from about 0.1 mg to about 1 g.

2. The composition according to claim 1, wherein the protective coating is selected from the group comprising hydrophilic polymers, hydrophobic polymers, natural polymers, synthetic polymers and mixtures thereof.

3. The composition according to claim 1, wherein at least one of the population of particles is an erodable formulation.

4. The composition according to claim 1, wherein at least one of the protective coatings comprises a modified-release coating.

5. The composition according to claim 1, wherein at least one of the protective coatings comprises a modified-release matrix coating.

6. The composition according to claim 2, wherein at least one portion of the composition further comprises an enhancer.

7. The composition according to claim 1 comprising a blend of the four populations of particles contained in a hard gelatin or soft gelatin capsule.

8. The composition according to claim 7, wherein the four populations of particles are in the form of mini-tablets and the capsule contains a mixture of the mini-tablets.

9. The composition according to claim 8, in the form of a tablet comprising a layer of compressed isosorbide dinitrate and hydralazine-containing particles.

10. The composition according to claim 9, wherein the four populations of particles are provided in a rapidly dissolving dosage form.

11. A method for the treatment of angina, ischaemic heart disease, arterial hypertension or related disease conditions comprising administering a therapeutically effective amount of a composition according to claim 1.

12. The composition according to claim 1, wherein the particles incorporating a modified-release coating comprise a pH-dependent polymer coating which is effective in releasing a pulse of the active ingredient following a time delay of two to twelve hours.

13. The composition according to claim 12, wherein the polymer coating comprises methacrylate copolymers.

14. The composition according to claim 4, wherein the modified-release coating comprises a mixture of methacrylate and ammonio methacrylate copolymers in a ratio sufficient to achieve a pulse of the active ingredients following a time delay.

15. The composition according to claim 14, wherein the ratio of methacrylate to ammonio methacrylate copolymers is between approximately 95:5 and 50:50.

16. The composition according to claim 1, wherein the hydralazine comprises hydralazine hydrochloride.

17. The composition according to claim 9, wherein the hydralazine comprises hydralazine hydrochloride.

18. The method according to claim 11, wherein the hydralazine comprises hydralazine hydrochloride.

* * * * *